(12) United States Patent
Cruz et al.

(10) Patent No.: US 9,271,639 B2
(45) Date of Patent: Mar. 1, 2016

(54) SURGICAL INTRODUCER AND ACCESS PORT ASSEMBLY

(71) Applicant: Covidien LP, Mansfield, MA (US)

(72) Inventors: Amos G. Cruz, Franklin, MA (US); Gregory Fischvogt, Hamden, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 287 days.

(21) Appl. No.: 13/755,244

(22) Filed: Jan. 31, 2013

(65) Prior Publication Data

US 2013/0225931 A1 Aug. 29, 2013

Related U.S. Application Data

(60) Provisional application No. 61/604,644, filed on Feb. 29, 2012.

(51) Int. Cl.
*A61B 17/00* (2006.01)
*A61B 1/32* (2006.01)
*A61B 17/34* (2006.01)

(52) U.S. Cl.
CPC ............... *A61B 1/32* (2013.01); *A61B 17/3423* (2013.01); *A61B 2017/3429* (2013.01)

(58) Field of Classification Search
CPC ................ A61B 1/32; A61B 17/3423; A61B 2017/3429; A61B 17/0218; A61B 17/0206; A61B 2017/3427; A61B 2017/3445; A61B 2017/3419; A61B 2017/3492; A61B 2017/3466; A61B 2019/306
See application file for complete search history.

(56) References Cited

U.S. PATENT DOCUMENTS

| | | | |
|---|---|---|---|
| 4,016,884 A | 4/1977 | Kwan-Gett |
| 4,112,932 A | 9/1978 | Chiulli |
| 4,183,357 A | 1/1980 | Bentley et al. |
| 4,402,683 A | 9/1983 | Kopman |
| 4,653,476 A | 3/1987 | Bonnet |

(Continued)

FOREIGN PATENT DOCUMENTS

| | | |
|---|---|---|
| EP | 0807416 | 11/1997 |
| EP | 0950376 | 10/1999 |

(Continued)

OTHER PUBLICATIONS

Extended European Search Report corresponding to EP 10 25 0638, mailed Aug. 5, 2010; (3 pp.).

(Continued)

*Primary Examiner* — Christopher Beccia
*Assistant Examiner* — Diana S Jones

(57) ABSTRACT

A surgical apparatus for permitting access to tissue includes an elongated introducer and a surgical port. The introducer includes an outer wall segment defining a longitudinal axis, a longitudinal port passage extending therethrough and a longitudinal slot in communication with the port passage. The introducer is dimensioned for at least partial introduction within an opening in tissue. The surgical port includes a port body mounted to the introducer with one of its leading and trailing ends disposed within the port passage and with the intermediate segment extending through the longitudinal slot and the other of the leading and trailing end external of the elongated introducer. The port body is dimensioned to be advanced within the port passage for deployment through the opening in the tissue and is adapted to transition from a compressed state to a released state.

9 Claims, 15 Drawing Sheets

(56) References Cited

U.S. PATENT DOCUMENTS

| | | |
|---|---|---|
| 4,863,430 A | 9/1989 | Klyce et al. |
| 4,863,438 A | 9/1989 | Gauderer et al. |
| 5,073,169 A | 12/1991 | Raiken |
| 5,082,005 A | 1/1992 | Kaldany |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,312,391 A | 5/1994 | Wilk |
| 5,330,486 A | 7/1994 | Wilk |
| 5,334,143 A | 8/1994 | Carroll |
| 5,345,927 A | 9/1994 | Bonutti |
| 5,366,478 A | 11/1994 | Brinkerhoff et al. |
| 5,375,588 A | 12/1994 | Yoon |
| 5,378,237 A | 1/1995 | Boussignac et al. |
| 5,391,156 A | 2/1995 | Hildwein et al. |
| 5,395,367 A | 3/1995 | Wilk |
| 5,437,683 A | 8/1995 | Neumann et al. |
| 5,460,170 A | 10/1995 | Hammerslag |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,522,791 A | 6/1996 | Leyva |
| 5,524,644 A | 6/1996 | Crook |
| 5,540,648 A | 7/1996 | Yoon |
| 5,545,179 A | 8/1996 | Williamson, IV |
| 5,577,993 A | 11/1996 | Zhu et al. |
| 5,601,581 A | 2/1997 | Fogarty et al. |
| 5,634,911 A | 6/1997 | Hermann et al. |
| 5,634,937 A | 6/1997 | Mollenauer et al. |
| 5,649,550 A | 7/1997 | Crook |
| 5,651,771 A | 7/1997 | Tangherlini et al. |
| 5,653,705 A | 8/1997 | de la Torre et al. |
| 5,672,168 A | 9/1997 | de la Torre et al. |
| 5,683,378 A | 11/1997 | Christy |
| 5,685,857 A | 11/1997 | Negus et al. |
| 5,713,858 A | 2/1998 | Heruth et al. |
| 5,713,869 A | 2/1998 | Morejon |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,746,764 A | 5/1998 | Green et al. |
| 5,782,817 A | 7/1998 | Franzel et al. |
| 5,785,715 A | 7/1998 | Schatz |
| 5,795,290 A | 8/1998 | Bridges |
| 5,803,921 A | 9/1998 | Bonadio |
| 5,810,712 A | 9/1998 | Dunn |
| 5,810,838 A | 9/1998 | Solar |
| 5,813,409 A | 9/1998 | Leahy et al. |
| 5,830,191 A | 11/1998 | Hildwein et al. |
| 5,836,871 A | 11/1998 | Wallace et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,860,966 A | 1/1999 | Tower |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,911,452 A | 6/1999 | Yan |
| 5,916,198 A | 6/1999 | Dillow |
| 5,941,898 A | 8/1999 | Moenning et al. |
| 5,944,735 A | 8/1999 | Green et al. |
| 5,957,913 A | 9/1999 | de la Torre et al. |
| 5,964,781 A | 10/1999 | Mollenauer et al. |
| 5,971,992 A | 10/1999 | Solar |
| 5,976,174 A | 11/1999 | Ruiz |
| 5,997,515 A | 12/1999 | de la Torre et al. |
| 6,009,614 A | 1/2000 | Morales |
| 6,017,355 A | 1/2000 | Hessel et al. |
| 6,018,094 A | 1/2000 | Fox |
| 6,024,736 A | 2/2000 | de la Torre et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,635 A | 5/2000 | Gianotti |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,534 B1 | 7/2001 | Butler et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence et al. |
| 6,527,787 B1 | 3/2003 | Fogarty et al. |
| 6,551,270 B1 | 4/2003 | Bimbo et al. |
| 6,558,371 B2 | 5/2003 | Dorn |
| 6,576,009 B2 | 6/2003 | Ryan et al. |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,706,050 B1 | 3/2004 | Giannadakis |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,745,445 B2 | 6/2004 | Spilka |
| 6,800,084 B2 | 10/2004 | Davison et al. |
| 6,811,546 B1 | 11/2004 | Callas et al. |
| 6,814,078 B2 | 11/2004 | Crook |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,945,932 B2 | 9/2005 | Caldwell et al. |
| 6,958,037 B2 | 10/2005 | Ewers et al. |
| 6,972,026 B1 | 12/2005 | Caldwell et al. |

(56) References Cited

U.S. PATENT DOCUMENTS

| | | | |
|---|---|---|---|
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,153,261 B2 | 12/2006 | Wenchell |
| 7,163,510 B2 | 1/2007 | Kahle et al. |
| 7,192,436 B2 | 3/2007 | Sing et al. |
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,766,824 B2 | 8/2010 | Jensen et al. |
| 7,798,898 B2 | 9/2010 | Luciano, Jr. et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,896,889 B2 | 3/2011 | Mazzocchi et al. |
| 7,909,760 B2 | 3/2011 | Albrecht et al. |
| 8,020,275 B2 | 9/2011 | Sarac et al. |
| 2001/0037053 A1 | 11/2001 | Bonadio et al. |
| 2002/0038077 A1 | 3/2002 | de la Torre et al. |
| 2002/0183594 A1 | 12/2002 | Beane et al. |
| 2003/0014076 A1 | 1/2003 | Mollenauer et al. |
| 2003/0105473 A1 | 6/2003 | Miller |
| 2003/0135091 A1 | 7/2003 | Nakazawa et al. |
| 2003/0236549 A1 | 12/2003 | Bonadio et al. |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0073090 A1 | 4/2004 | Butler et al. |
| 2004/0088038 A1 | 5/2004 | Dehnad et al. |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0240082 A1 | 10/2005 | Bonadio et al. |
| 2005/0241647 A1 | 11/2005 | Nguyen et al. |
| 2005/0267419 A1 | 12/2005 | Smith |
| 2005/0288558 A1 | 12/2005 | Ewers et al. |
| 2006/0020241 A1 | 1/2006 | Piskun et al. |
| 2006/0030755 A1 | 2/2006 | Ewers et al. |
| 2006/0071432 A1 | 4/2006 | Staudner |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0229501 A1 | 10/2006 | Jensen et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0270911 A1 | 11/2006 | Voegele et al. |
| 2007/0088202 A1 | 4/2007 | Albrecht et al. |
| 2007/0088204 A1 | 4/2007 | Albrecht et al. |
| 2007/0088241 A1 | 4/2007 | Brustad et al. |
| 2007/0088258 A1 | 4/2007 | Wenchell et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0225569 A1 | 9/2007 | Ewers et al. |
| 2007/0232864 A1* | 10/2007 | Sharp ............... A61B 17/02 600/227 |
| 2007/0270654 A1* | 11/2007 | Pignato ............ A61B 17/02 600/208 |
| 2007/0270882 A1 | 11/2007 | Hjelle et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097350 A1 | 4/2008 | Bell et al. |
| 2008/0161826 A1 | 7/2008 | Guiraudon |
| 2008/0200767 A1 | 8/2008 | Ewers et al. |
| 2008/0255519 A1 | 10/2008 | Piskun et al. |
| 2008/0319261 A1 | 12/2008 | Lucini |
| 2009/0012477 A1 | 1/2009 | Norton et al. |
| 2009/0093752 A1 | 4/2009 | Richard et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0187079 A1 | 7/2009 | Albrecht et al. |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2009/0326461 A1 | 12/2009 | Gresham |
| 2010/0063452 A1 | 3/2010 | Edelman et al. |
| 2010/0100043 A1 | 4/2010 | Racenet |
| 2010/0240960 A1 | 9/2010 | Richard |
| 2010/0249516 A1 | 9/2010 | Shelton, IV et al. |
| 2010/0249524 A1* | 9/2010 | Ransden ........... A61B 17/3423 600/207 |
| 2010/0312061 A1 | 12/2010 | Hess et al. |
| 2011/0021877 A1* | 1/2011 | Fortier ............. A61B 17/3423 600/206 |

FOREIGN PATENT DOCUMENTS

| | | |
|---|---|---|
| EP | 1312318 | 5/2003 |
| EP | 1774918 | 4/2007 |

(56) References Cited

FOREIGN PATENT DOCUMENTS

| | | |
|---|---|---|
| EP | 2044889 | 4/2009 |
| EP | 2044897 | 4/2009 |
| EP | 2098182 | 9/2009 |
| EP | 2181657 | 5/2010 |
| EP | 2289438 | 3/2011 |
| WO | WO 93/14801 | 8/1993 |
| WO | WO 94/04067 | 3/1994 |
| WO | WO 96/36283 | 11/1996 |
| WO | WO 97/33520 | 9/1997 |
| WO | WO 97/42889 | 11/1997 |
| WO | WO 99/16368 | 4/1999 |
| WO | WO 99/22804 | 5/1999 |
| WO | WO 00/32120 | 6/2000 |
| WO | WO 01/08581 | 2/2001 |
| WO | WO 01/32116 | 5/2001 |
| WO | WO 01/49363 | 7/2001 |
| WO | WO 02/07611 | 1/2002 |
| WO | WO 03/034908 | 5/2003 |
| WO | WO 03/071926 | 9/2003 |
| WO | WO 2004/043275 | 5/2004 |
| WO | WO 2004/054456 | 7/2004 |
| WO | WO 2004/075741 | 9/2004 |
| WO | WO 2004/075930 | 9/2004 |
| WO | WO 2006/019723 | 2/2006 |
| WO | WO 2006/100658 | 9/2006 |
| WO | WO 2006/110733 | 10/2006 |
| WO | WO 2006/115893 | 11/2006 |
| WO | WO 2008/011358 | 1/2008 |
| WO | WO 2008/015566 | 2/2008 |
| WO | WO 2008/042005 | 4/2008 |
| WO | WO 2008/093313 | 8/2008 |
| WO | WO 2008/103151 | 8/2008 |
| WO | WO 2008/121294 | 10/2008 |
| WO | WO 2009/036343 | 3/2009 |

OTHER PUBLICATIONS

Extended European Search Report corresponding to EP 10 25 1317, mailed Oct. 25, 2010; (5 pp.).
Extended European Search Report corresponding to EP 13156882.6, completed Jun. 3, 2013 and mailed Jun. 11, 2013; (9 pp).

* cited by examiner

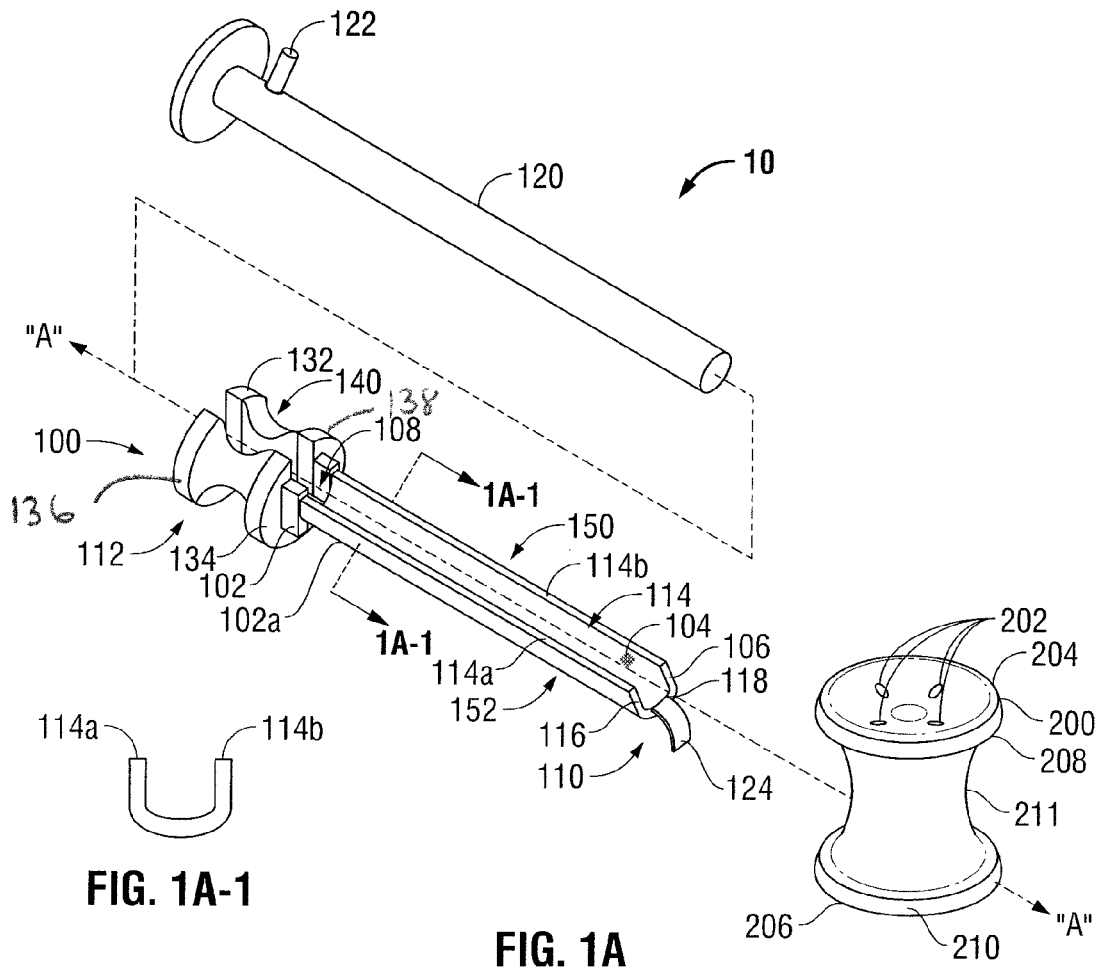
FIG. 1A-1
FIG. 1A
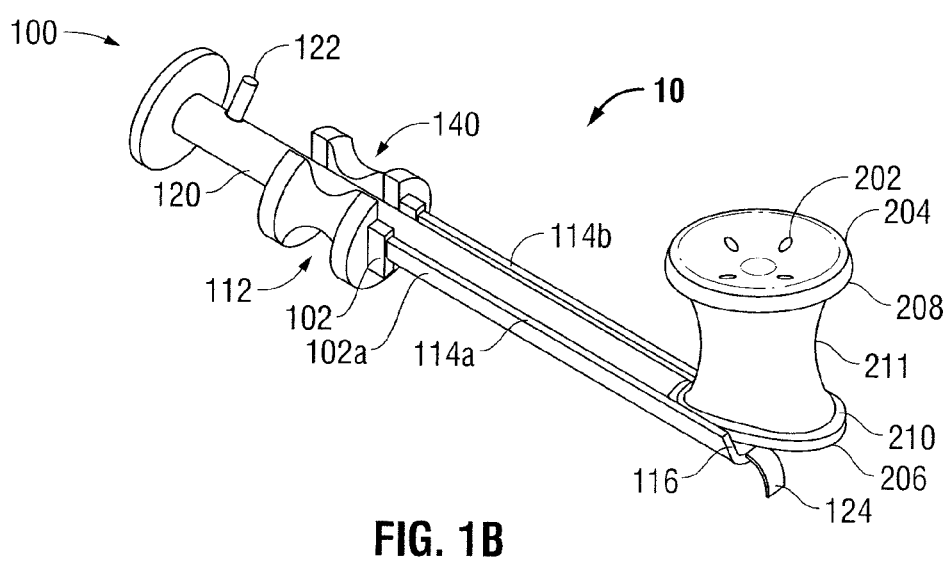
FIG. 1B

SURGICAL INTRODUCER AND ACCESS PORT ASSEMBLY

CROSS REFERENCE TO RELATED APPLICATION

The present application claims the benefit of and priority to U.S. Provisional Application Ser. No. 61/604,644, filed on Feb. 29, 2012, the entire contents of which are incorporated herein by reference.

BACKGROUND

1. Technical Field

The present disclosure relates to surgical access ports, and, more particularly, relates to an introducer and associated compressible port adapted to facilitate positioning of the port within tissue in connection with a laparoscopic surgical procedure.

2. Related Art

Single Port Access (SPA™) surgery, also known as Single Incision Laparoscopic Surgery (SILS™) or One Port Umbilical Surgery (OPUS) or Natural Orifice TransUmbilical Surgery (NOTUS), is an advanced minimally invasive surgical procedure in which a clinician operates almost exclusively through a single entry point, typically a port positioned in a patient's navel. Surgical procedures of this type are like many laparoscopic surgeries in that the patient is under general anesthesia, insufflated and laparoscopic visualization is utilized. Typically, the port is inserted through an incision (e.g., 20 mm incision) via a surgical instrument, e.g., a port introducer device in the form of a Kelly clamp.

Once a skin incision is made inferior to a patient's umbilicus, the patient is typically prepared for laparoscopic surgery using the Kelly clamp method. The Kelly clamp method involves spreading, separating, and dividing subcutaneous tissue (i.e., dissection). A surgeon's ability to properly place a port, e.g., a SILS™ port, may present practical challenges due to the limited length of the Kelly clamp's arm and handle. Furthermore, since the device is held in the palm of a surgeon's hand, sufficient visibility may not be possible using this technique without overly dilating the incision and compromising the seal. Not only is proper placement of a SILS™ port challenging using the Kelly clamp method, but removal of the Kelly clamp after successful installation may also be difficult. In addition, improper loading of the Kelly clamp may result in the clamp's metal tips coming into unintentional contact with the surgical area, which may result in injury including scarring, pain, and/or longer convalescence.

SUMMARY

Accordingly, a surgical apparatus for permitting access to tissue includes an elongated introducer and a surgical port. The introducer includes an outer wall segment defining a longitudinal axis and a longitudinal port passage extending therethrough. The outer wall segment has a longitudinal slot in communication with the port passage. The elongated introducer is dimensioned for at least partial introduction within an opening in tissue. The surgical port includes a port body having leading and trailing ends, an intermediate segment disposed between the leading and trailing ends and at least one passageway for reception and passage of a surgical instrument. The port body is mounted to the elongated introducer with one of the leading and trailing ends disposed within the port passage and with the intermediate segment extending through the longitudinal slot and the other of the leading and trailing end external of the elongated introducer. The port body is dimensioned to be advanced within the port passage for deployment through the opening in the tissue as generally directed by the elongated introducer. The port body comprising a compressible material and is adapted to transition from a compressed state when mounted to the elongated introducer to a released state when deployed from the elongated introducer.

The surgical elongated introducer may define introducer leading and trailing ends, and further includes a retractor segment adjacent the introducer leading end. The retractor segment is dimensioned and configured to retract tissue surrounding the opening. The retractor segment may define an arcuate profile. The outer wall segment of the elongated introducer is substantially arcuate along a major portion of the length thereof. The retractor segment may define a general hook-shape and is arranged in oblique relation with the longitudinal axis.

A pusher member may be at least partially disposed within the longitudinal port passage of the elongated introducer. The pusher member may be adapted for longitudinal advancement to engage and deploy the port body from the introducer and within the opening in tissue. The elongated introducer may include a handle mounted to the outer wall segment dimensioned for engagement by the user. The elongated introducer may be substantially rigid, flexible or include both rigid and flexible portions. At least a portion of the longitudinal slot is coated with a lubricious material.

The outer wall segment of the elongated introducer may include first and second movable segments. Thee first and second movable segments may be adapted for movement between a generally open position and a generally approximated position, wherein, when in the open position, the one of the leading and trailing ends of the port body is positionable within the port passage, and, when in the approximated position, the port body is moved to the compressed state with the one of the leading and trailing ends disposed within the port passage, the intermediate segment extending through the longitudinal slot and the other of the leading and trailing end external of the elongated introducer. The first and second movable segments may be adapted for pivotal movement relative to each other.

The elongated introducer may include a substantially flexible portion and a rigid portion. The substantially flexible portion may be movable between a first position for securing the port therein to a second position for facilitating removal of the elongated introducer from the opening in the tissue. The substantially flexible portion may be dimensioned to extend substantially the length of the rigid portion.

A retrieval structure may be operably coupled to the distal end of the elongated introducer. The retrieval structure may be selected from the group consisting of a suture, string and filament.

BRIEF DESCRIPTION OF THE DRAWINGS

Embodiments of the disclosure will be described with reference to the accompanying drawings in which.

Figure 1C:
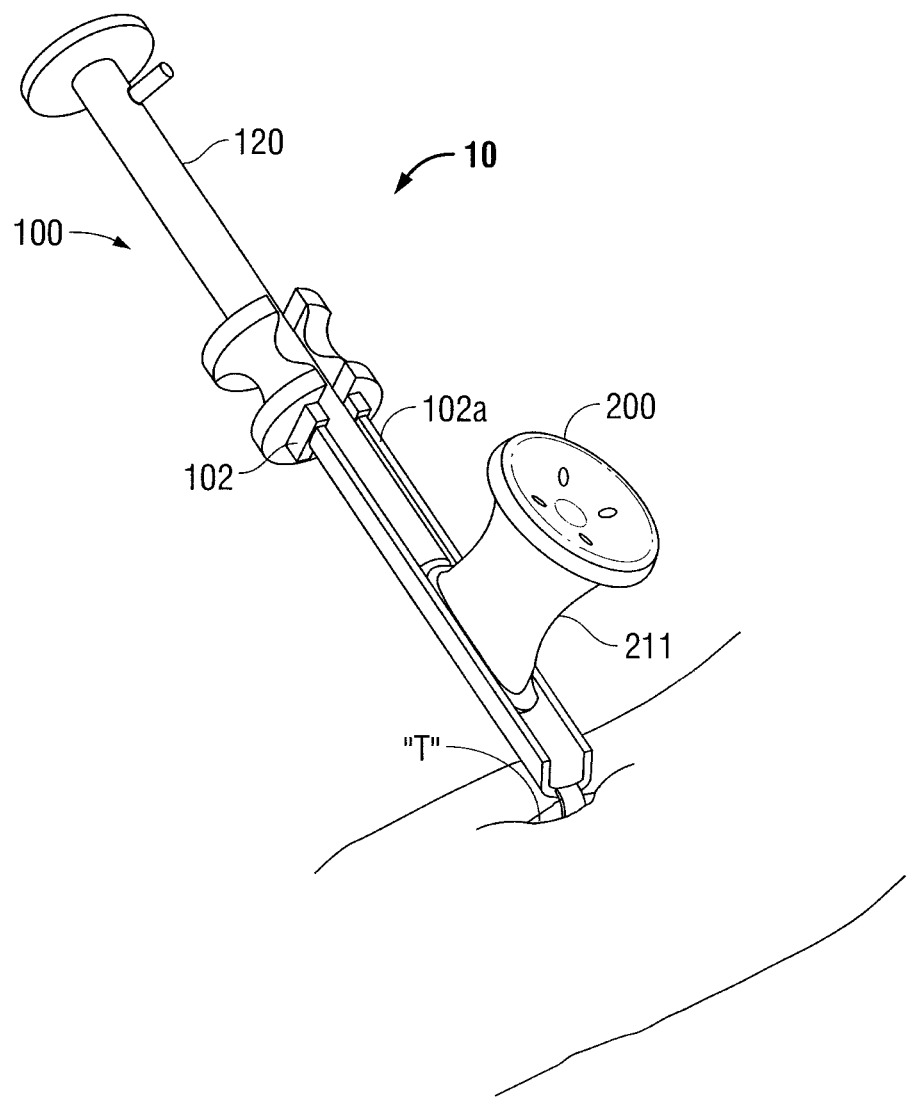
FIG. 1A is a perspective view of a port and port introducer in accordance with an embodiment of the present disclosure.
Figure 1D:
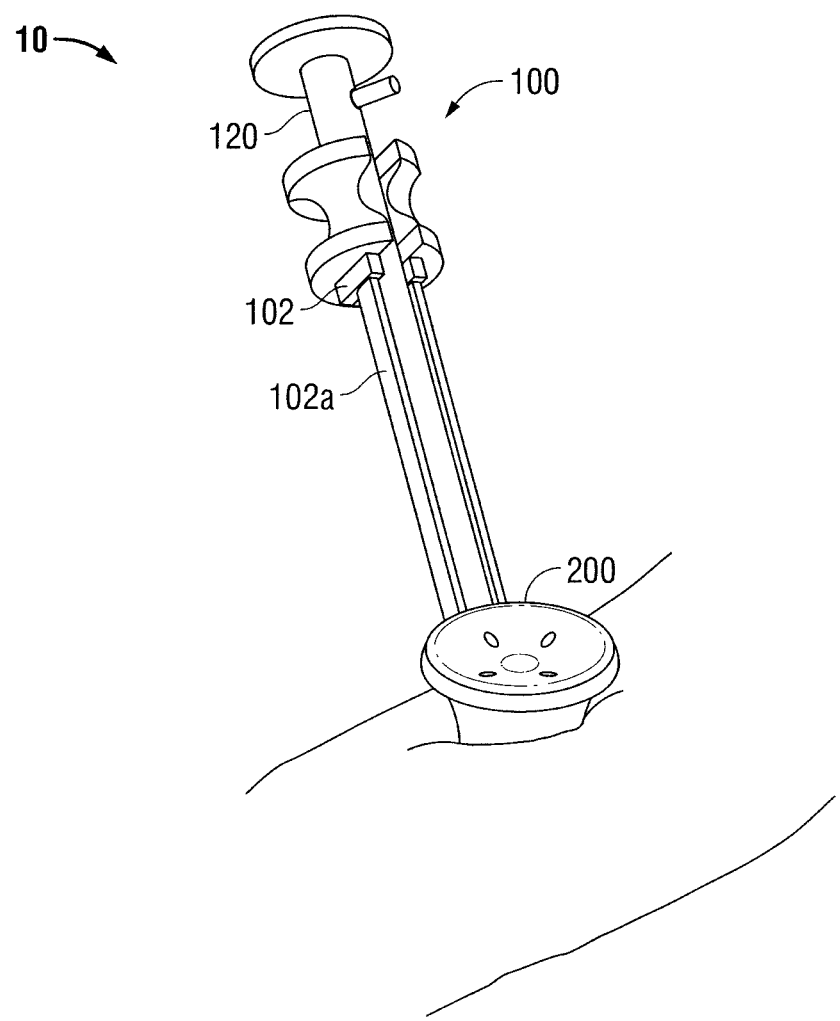
Figure 2A:
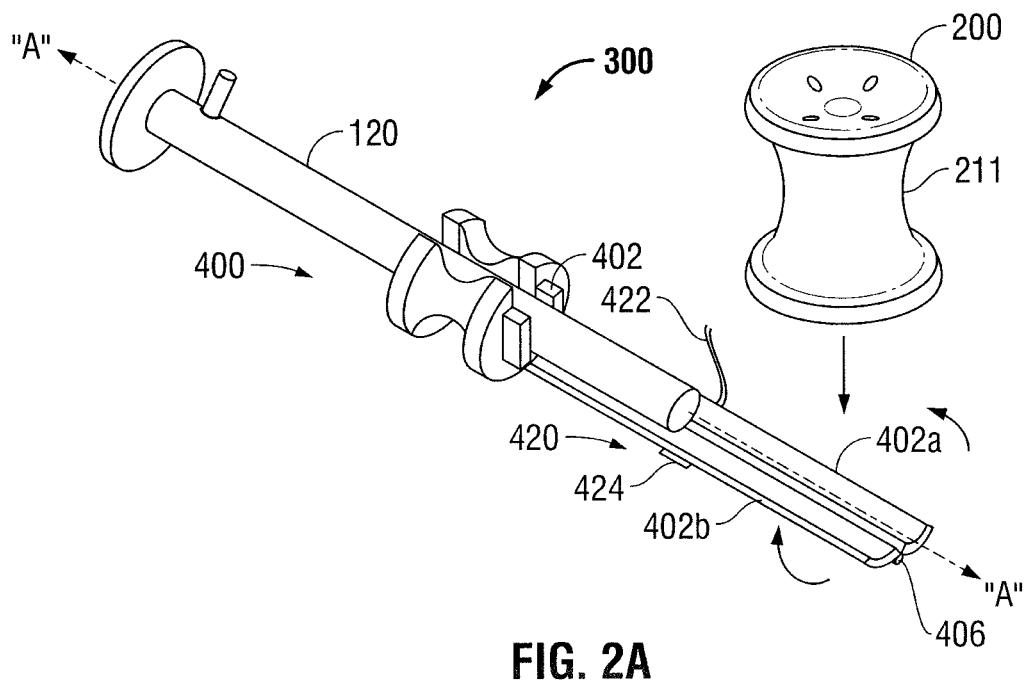
Figure 2B:
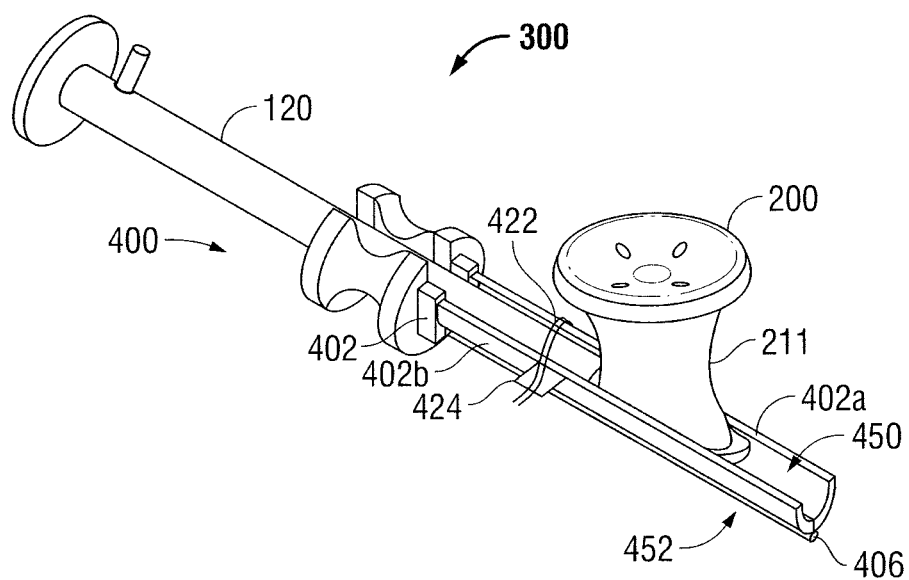
Figure 2C:
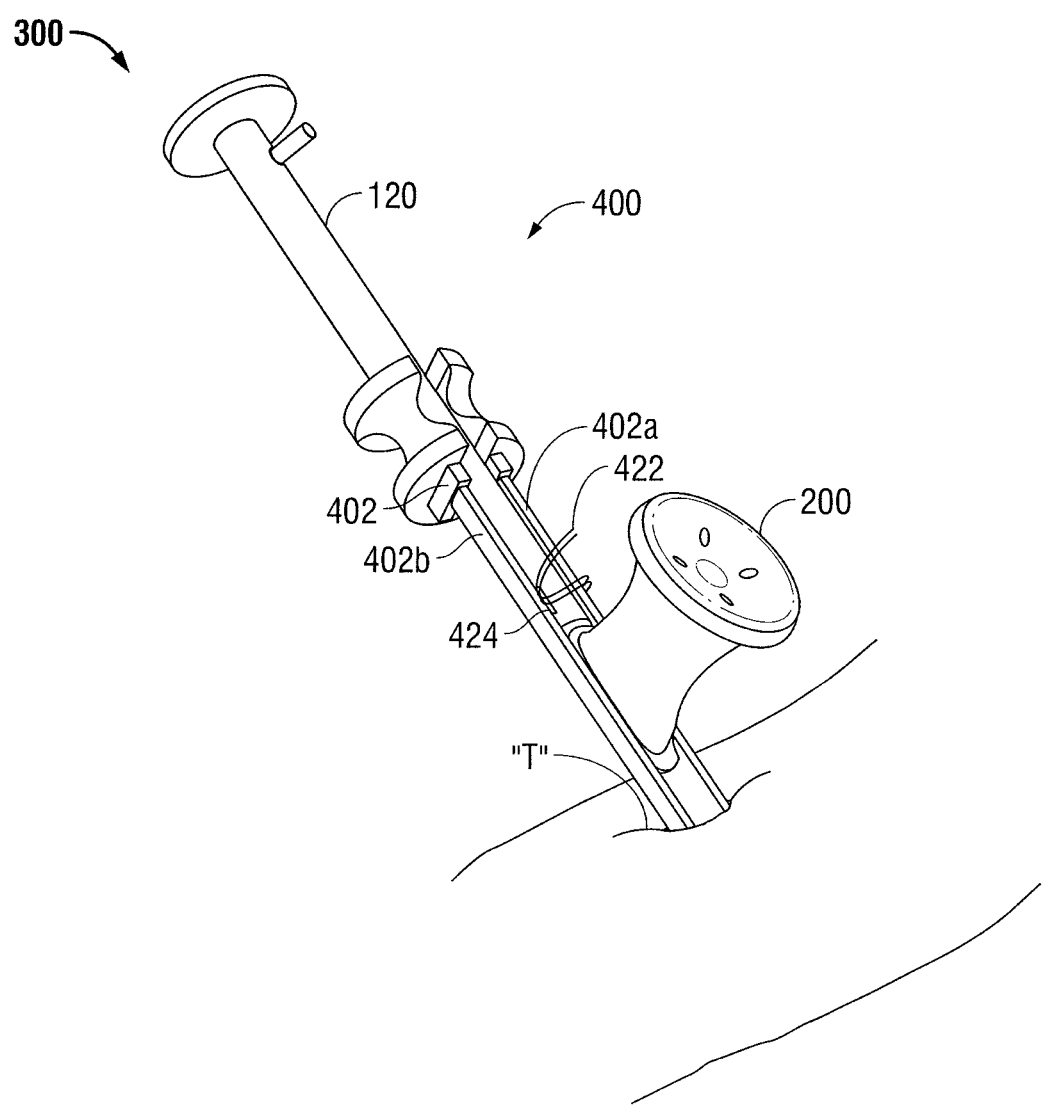
Figure 2D:
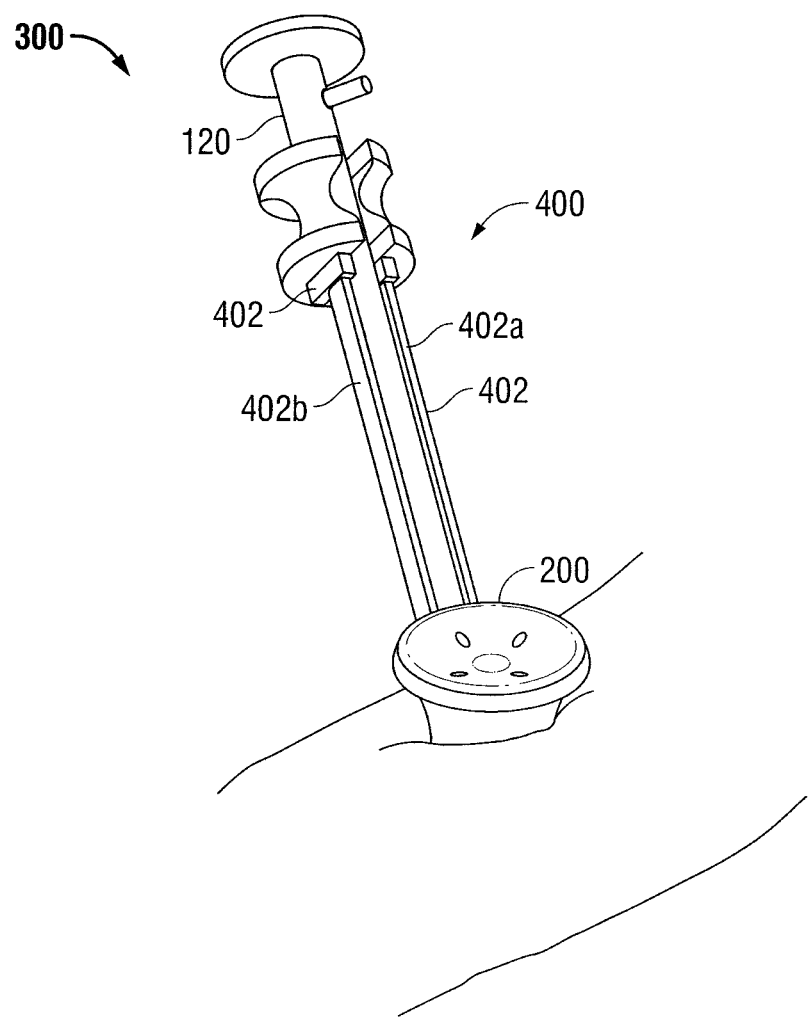
Figure 3A:
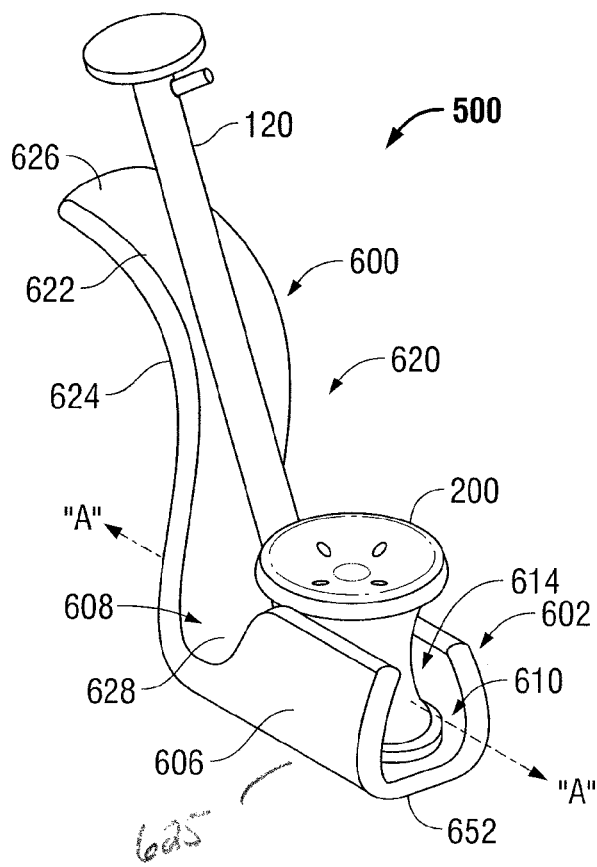
Figure 3B:
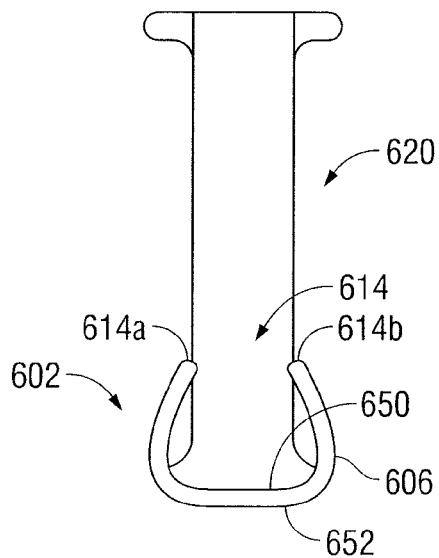
Figure 3C:
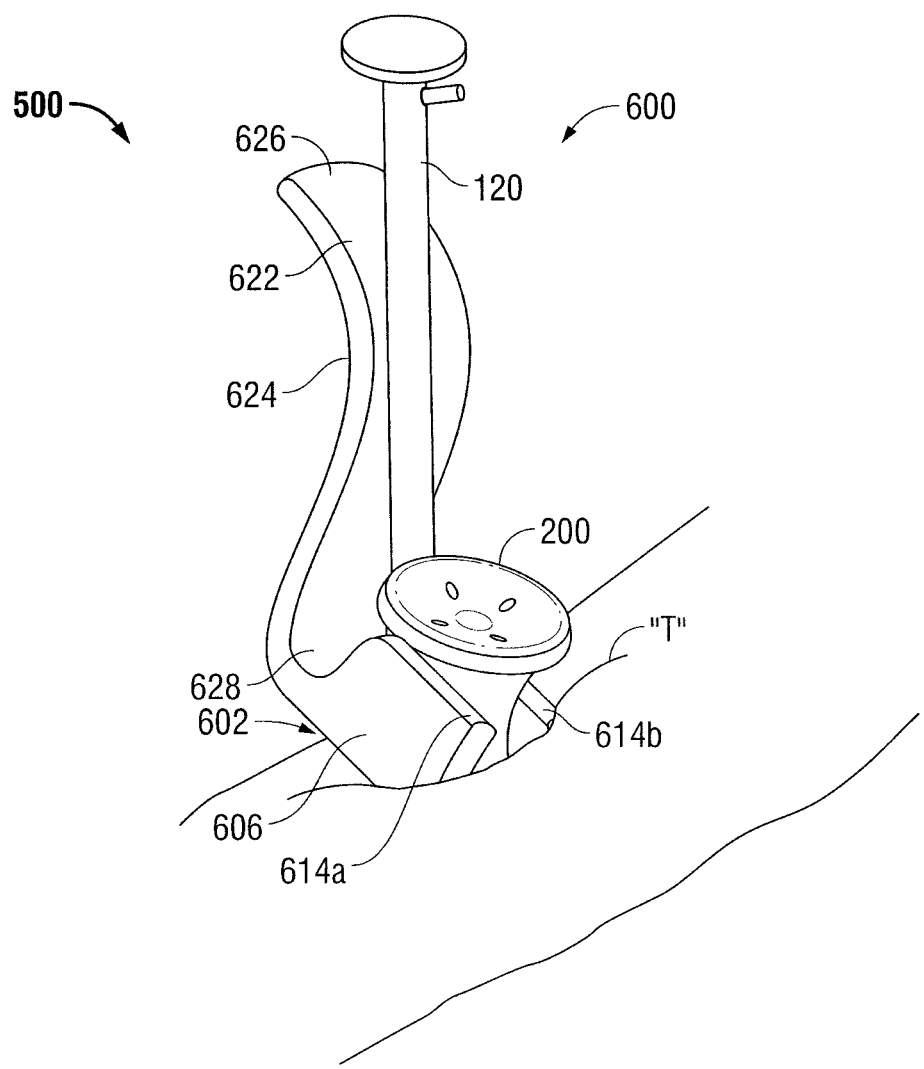
Figure 3D:
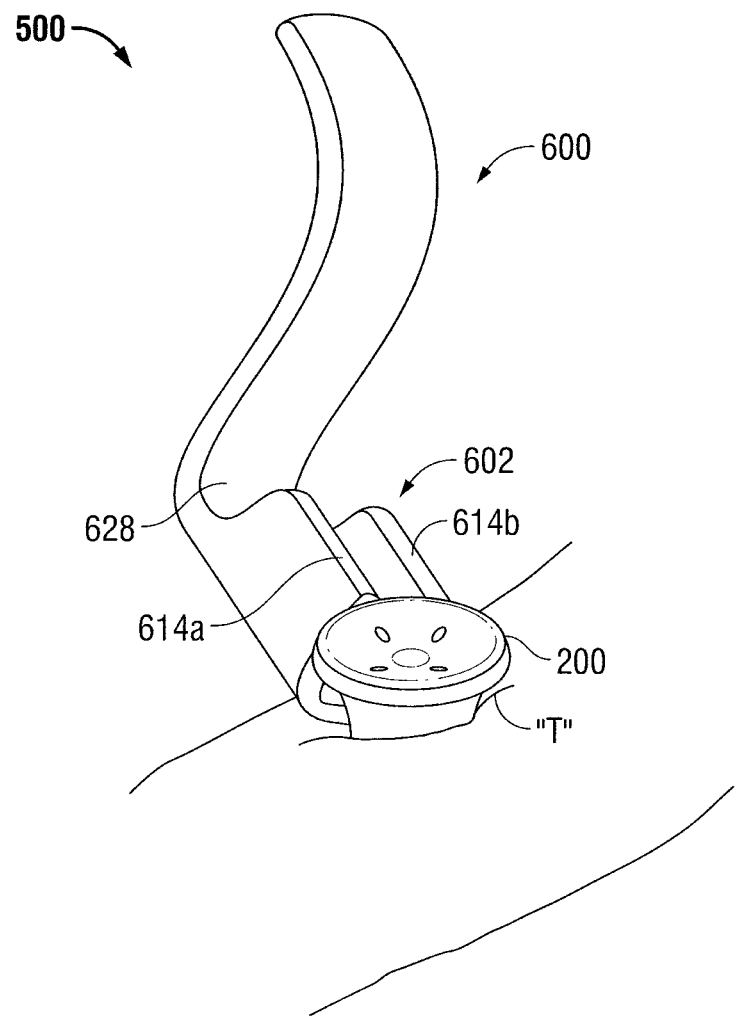
Figure 4A:
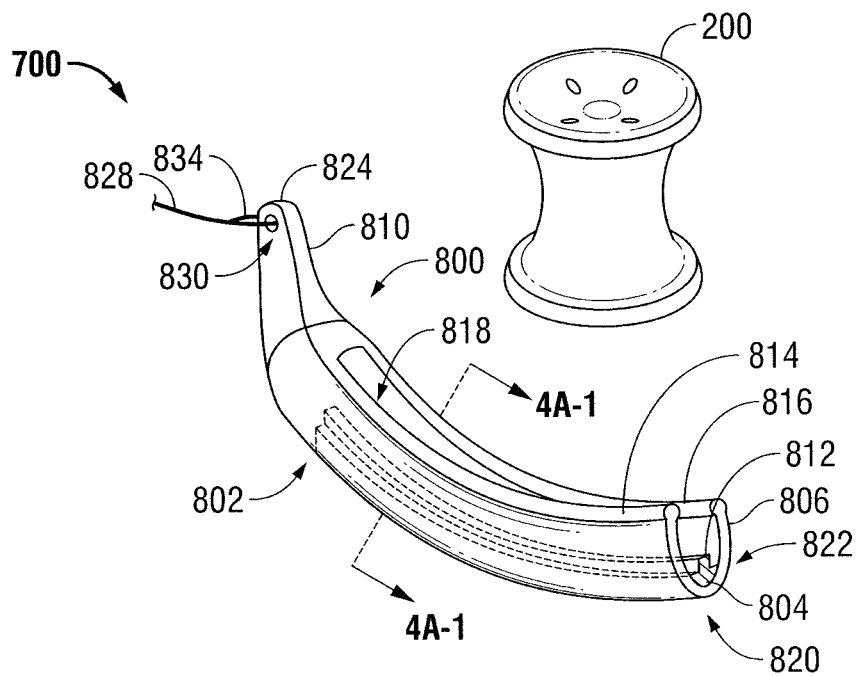
Figures 1, 4A:
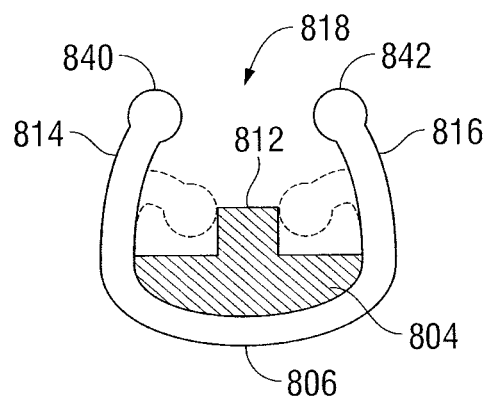
Figure 4B:
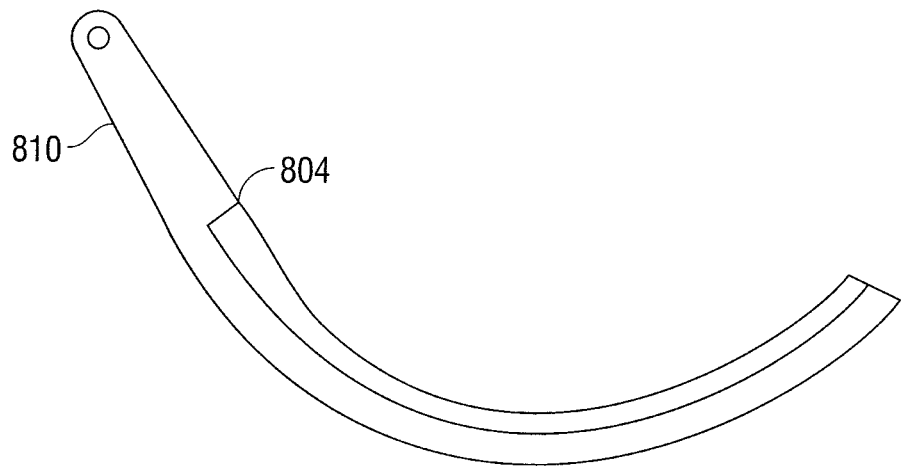
Figure 4C:
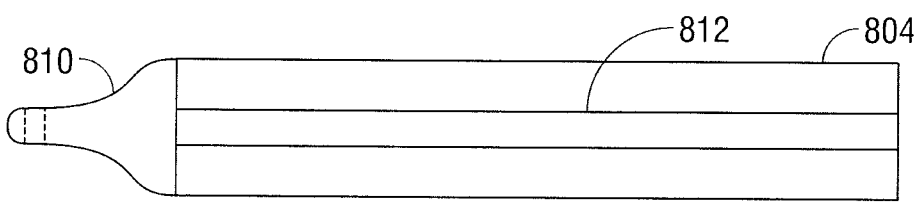
Figure 4D:
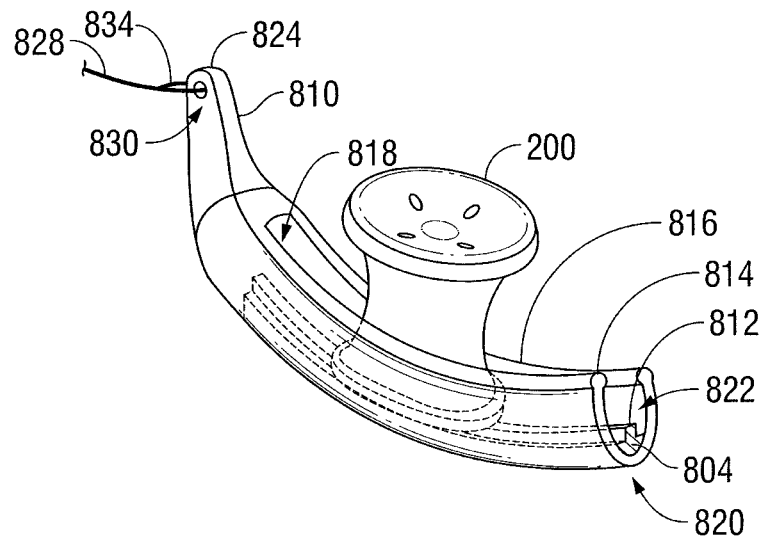
Figure 4E:
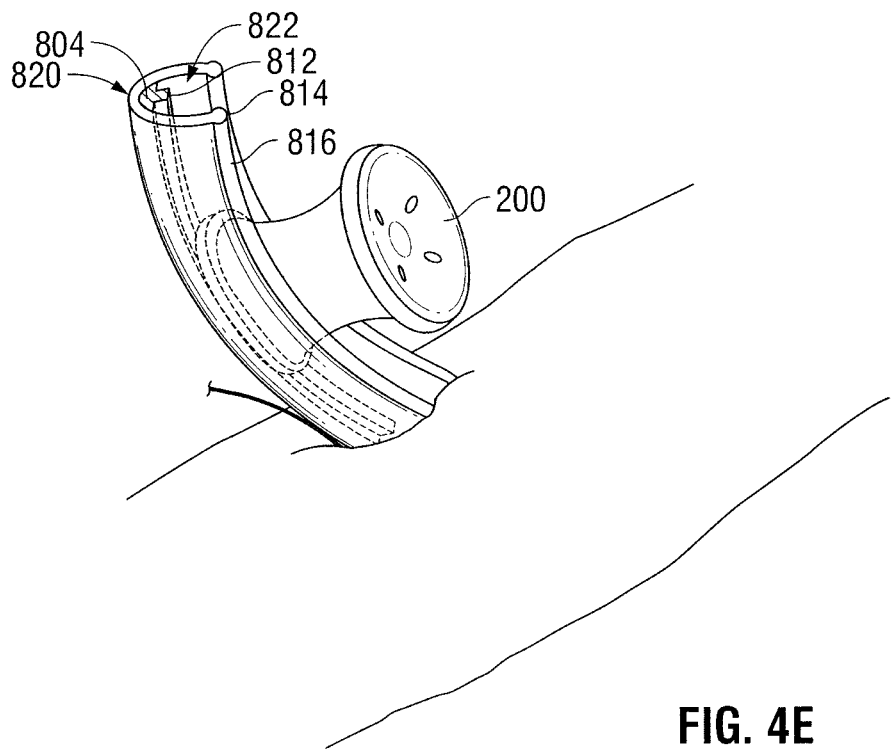
Figure 4F:
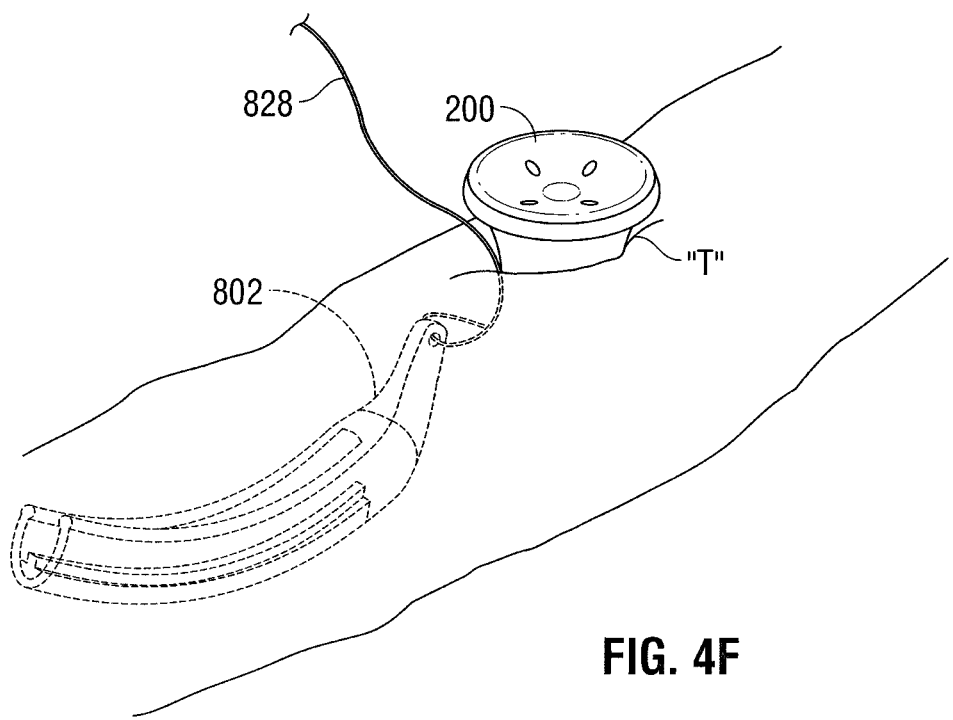
Figure 4G:
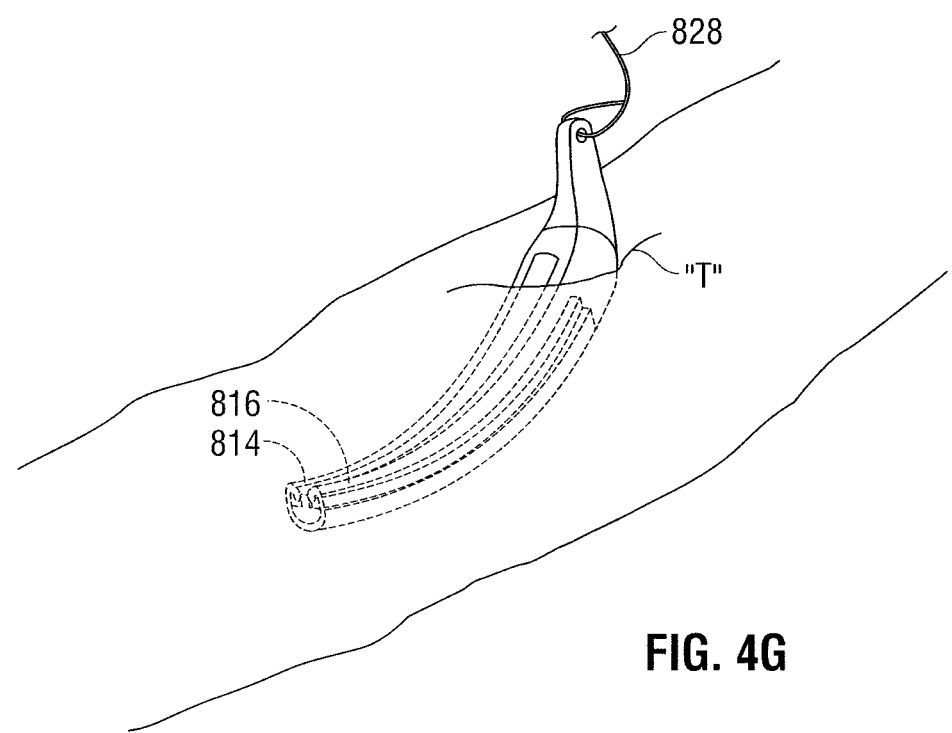
Figure 4H:
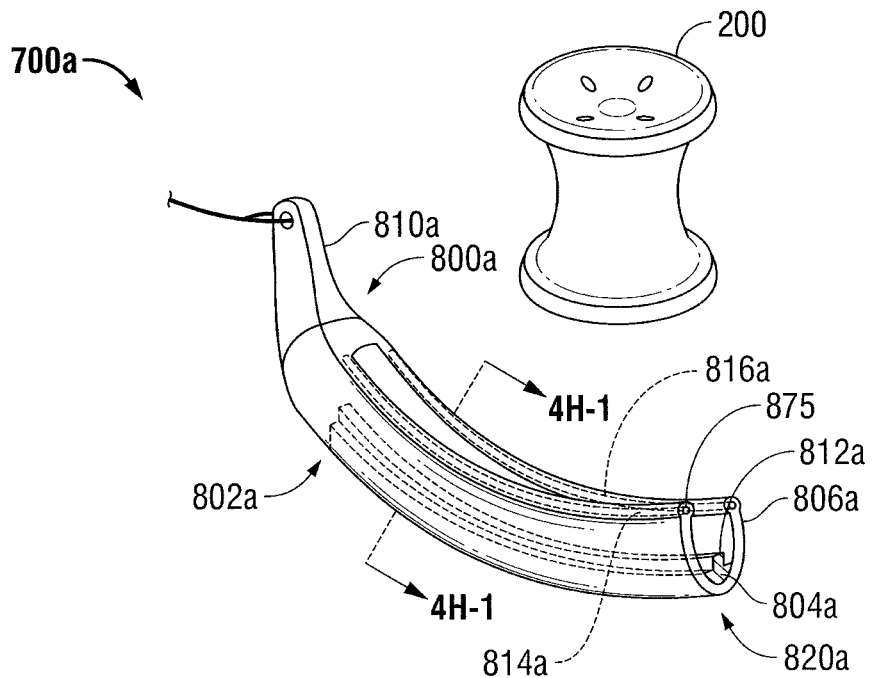
Figures 1, 4H:
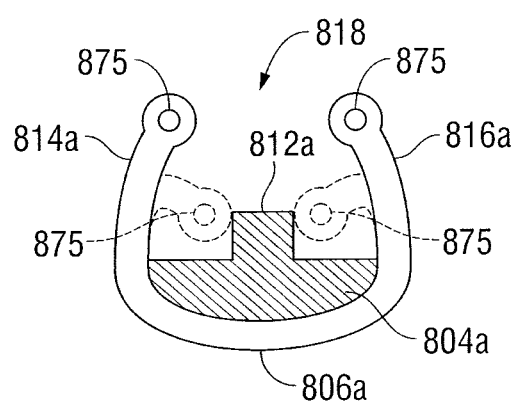
Figure 4I:
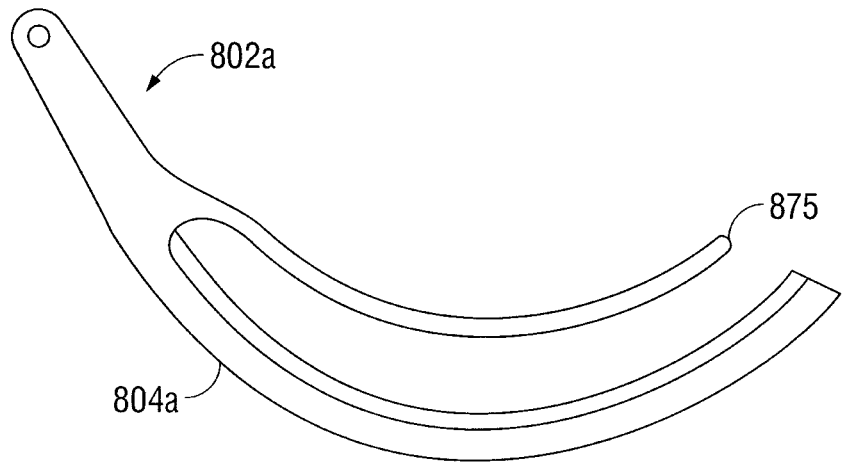
Figure 4J:
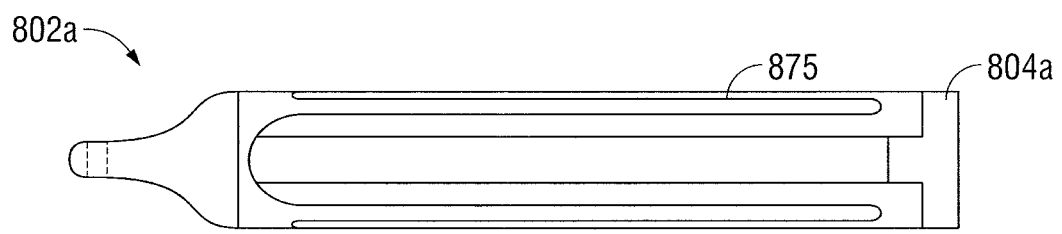

FIG. $1A_{-1}$ is a cross-sectional view taken along line segment "$1A_{-1}$-$1A_{-1}$" of FIG. 1A;

FIG. 1B is a perspective view illustrating the port being loaded into the port introducer depicted in FIG. 1A;

FIG. 1C is a perspective view illustrating the port introducer accessing tissue and the port loaded within the port introducer;

FIG. 1D is a perspective view illustrating the port securely positioned within tissue of a patient;

FIG. 2A is a perspective view of a port and port introducer in accordance with an alternate embodiment of the present disclosure;

FIG. 2B is a perspective view illustrating the port being loaded into the port introducer mechanism depicted in FIG. 2A;

FIG. 2C a perspective view illustrating the port introducer accessing tissue and the port loaded within the port introducer;

FIG. 2D a perspective view illustrating the port securely positioned within tissue of a patient;

FIG. 3A is a perspective view illustrating a port and port introducer in accordance with an another embodiment of the present disclosure;

FIG. 3B is a front view of the port introducer depicted in FIG. 3A;

FIG. 3C is a perspective view illustrating the port introducer accessing tissue and the port loaded within the port introducer;

FIG. 3D is a perspective view illustrating the port securely positioned within tissue and the port introducer extracted from tissue;

FIG. 4A is a perspective view of a port and port introducer in accordance with an embodiment of the present disclosure;

FIG. $4A_{-1}$ is a cross-sectional view taken along line segment "$4A_{-1}$-$4A_{-1}$" of FIG. 4A;

FIG. 4B is a side view of a rigid portion associated with the port introducer depicted in FIG. 4A;

FIG. 4C is a top elevational view of the rigid portion depicted in FIG. 4B;

FIG. 4D is a perspective view illustrating the port being loaded into the port introducer depicted in FIG. 4A;

FIG. 4E is a perspective view illustrating the port introducer accessing tissue and the port loaded within the port introducer;

FIG. 4F is a perspective view illustrating the port securely positioned within tissue of a patient;

FIG. 4G is a perspective view illustrating the port removed from tissue and the introducer being extracted from tissue;

FIG. 4H is a perspective view of a port introducer in accordance with an embodiment of the present disclosure;

FIG. $4H_{-1}$ is a cross-sectional view taken along line segment "$4H_{-1}$-$4H_{-1}$" of FIG. 4H;

FIG. 4I is a side view of a rigid portion associated with the port introducer depicted in FIG. 4H; and FIG. 4J is a top elevational view of the rigid portion depicted in FIG. 4I.

DETAILED DESCRIPTION OF THE EMBODIMENTS

Particular embodiments of the present disclosure will be described herein with reference to the accompanying drawings. In the following description, well-known functions or constructions are not described in detail to avoid obscuring the present disclosure in unnecessary detail. As shown in the drawings and as described throughout the following descriptions, and as is traditional when referring to relative positioning on an object, the term "proximal" refers to the end of the device that is closer to the user and the term "distal" refers to the end of the apparatus that is further from the user.

The port introducers according to the present disclosure are configured to facilitate the introduction of an access port, e.g., a foam port, within a surgical incision of a patient. It is envisioned that the port introducers may be used in connection with other surgical procedures utilizing natural or formed openings in a body cavity of a patient. Embodiments of the present disclosure are illustrated in FIGS. 1A-4J.

With reference to FIGS. 1A-1D, and initially with reference to FIG. 1A, an embodiment of a port introducer 10 is shown. In the embodiment illustrated in FIGS. 1A-1D, port introducer 10 includes an introducer assembly 100 that is suitable for use with a surgical foam port 200. The port introducer 10 and foam port 200 may be manufactured and sold separately or provided as a kit.

Introducer assembly 100 includes a substantially rigid elongated introducer or housing 102 dimensioned for at least partial introduction within an opening in tissue. In the embodiment illustrated in FIG. 1A-1D, housing 102 is of a unitary construction formed by any suitable manufacturing methods including but not limited to injection molding, overmolding, etc. Housing 102 may be formed from any suitable biocompatible material including rigid such as stainless steel, titanium, polymeric material and/or a resilient elastomeric material. In embodiments, housing 102, or portion thereof, may be coated with or formed from a lubricious material 104. More particularly, in the embodiment illustrated in FIGS. 1A-1D, an internal surface 106 is coated with a layer of one or more types of fluoropolymers including without limitation, polytetrafluoroethylene (a.k.a. PTFE or Teflon®, manufactured by the E.I. du Pont de Nemours and Co. of Wilmington, Del., USA), see FIG. 1A, for example. Coating internal surface 106 of housing 102 with a lubricious material 104 decreases the coefficient of kinetic friction (μk) between the internal surface 106 and the port 200 and, thus, facilitates movement of the port 200 through housing 102. In embodiments, the lubricious material 104 may be selected from the group consisting of polytetrafluoroethylene (PTFE), perfluoroalkoxy polymer resin (PFA), fluorinated ethylene-propylene (FEP).

Housing 102 is configured to receive, compress and releasably secure the port 200 therein. With this purpose in mind, housing 102 includes an outer wall segment 102a defining a longitudinal axis "A-A" and a surgical port 200 passageway therethrough. Outer wall segment 102a includes a slotted tube configuration with open proximal (or trailing) and distal (or leading) ends 108 and 110, respectively. Housing 102 includes a proximal face 150 and a distal face 152. In an embodiment, the proximal end 108 may be closed. A longitudinal slot 114 is disposed adjacent the proximal face 150 and may extend at least partially along a length of the housing 102. In the embodiment illustrated in FIGS. 1A-1D, the longitudinal slot 114 extends along the length of the housing 102 from the proximal end 108 to the distal end 110 such that the housing 102 includes a generally "C" like configuration (see FIG. $1A_{-1}$). A pair of top edges 114a and 114b extend along the length of the longitudinal slot 114 and run parallel to the longitudinal axis "A-A" (see FIG. $1A_{-1}$ in conjunction with FIG. 1B). The longitudinal slot 114 facilitates loading and unloading of the port 200 into the distal end 110 of the housing 102. The longitudinal slot 114 is proportioned to move the port 200 toward a compressed state as the port 200 is pushed within the longitudinal slot 114 from the distal end 110 of the housing 102 toward the proximal end 108 of the housing 102. Distal end 110 includes a leading edge 116 that is angled or slanted with respect to top edges 114a and 114b. More particularly, the leading edge 116 extends from a distal portion of the top edges 114a and 114b at an angle culminating at a distal insertion tip 118. The angled leading edge 116 and distal tip 118 facilitate loading and unloading of the port 200 into the housing 102 and positioning the housing 102 into a tissue tract. One or more types of structure 124 configured to manipulate tissue may be operably associated with the distal end 110. More particularly, distal tip 118 includes a retractor having a generally "hook" like shape 124 (or other suitable structure), see FIG. 1B. In this instance, the retractor 124 may be employed to retract tissue, such as, for example, prior to insertion of the housing 102 into the tissue tract (FIG. 1C). Retractor 124 includes a generally arcuate or curved configuration and extends distally from the distal end 110 of the housing 102 in a generally oblique relation with the longitudinal axis "A-A." The retractor 124 may be a separate structure operably coupled to the housing 102 at the distal end 110 thereof, or the retractor 124 may be monolithically formed with the distal tip 118. For example, a portion, e.g., the distal face 152, of the distal tip 118 may curve toward the proximal end 108 forming the hook 124.

In an embodiment, a gripping device or handle assembly may be operably coupled to the proximal end 108. In the embodiment illustrated in FIGS. 1A-1D, proximal end 108 includes a handle assembly 112. Handle assembly 112 may operably couple to the proximal end 108 by any suitable means. For example, handle assembly 112 may be monolithically formed with the proximal end 108 or may be removably attached to the proximal end via a press or friction fit. Handle 112 assembly includes a generally "C" like configuration when viewed in cross-section. Handle assembly 112 includes proximal and distal ends 132 and 134, respectively, each having a respective flange 136 and 138. A circular recess 140 is defined between the flanges 136 and 138. The recess 140 is configured to receive one or more fingers of a user. The recess provides additional leverage for the user and, thus, facilitates a user in pushing the port 200 through the longitudinal slot 114 and from the housing 102. While the drawings depict the longitudinal slot 114 extending through the handle assembly, it is within the purview of the present disclosure to have the longitudinal slot not extend through the handle assembly 112.

In the embodiment illustrated in FIGS. 1A-1D, a surgical instrument 120 may be employed to push out, i.e., deploy the surgical port 200 from the distal end 110 of the housing 102 when the housing 102 is positioned within a tissue tract or an incision of the patient (FIG. 1D). To this end, a surgical instrument in the form of push rod 120 or the like is receivable within the handle assembly 112 and movable within at least a portion of the housing 102. In the embodiment illustrated in FIGS. 1A-1D, the push rod 120 includes a guide pin 122 that is configured to move within the longitudinal slot 114. When the push rod 120 is employed to push out, i.e., deploy the surgical port 200 from the distal end 110 of the housing 102, the recess provides additional leverage to the user and, thus, allows a user to deploy the surgical port 200 from the distal end 110 of the housing 102 with one hand.

As noted above, port introducer assembly 100 is suitable for use with a surgical foam port 200. A brief description of a surgical port 200, and operative features associated therewith, now follows.

Port 200 is of the foam type and is adapted to transition from a normally non-compressed or relaxed state or condition (FIGS. 1A and 1D) for affixing the port 200 within an incision or opening of a patient to a compressed condition (FIG. 1C) when mounted to the housing 102 for inserting the port 200 within the incision of a patient. Port 200 may be formed from any suitable bio-compatible material, such as, for example, a thermoplastic elastomer. Part 200 is configured to receive one or more types of surgical instruments, e.g., laparoscopic and/or endoscopic instruments. With this purpose in mind, port 200 includes a port body 211 and may include one or more passageways or openings 202 that extend from a proximal (or trailing) end 204 of the foam port 200 to the distal (or leading) end 206 of the foam port 200. Openings 202 may have any suitable geometric configuration. As shown in the representative drawings, openings 202 have a generally circular configuration. Trailing end 204 includes a generally circumferential configuration and includes a flange 208 that is configured to contact an outer surface of an abdominal wall of a patient (FIG. 1D). Likewise, leading end 206 includes a generally circumferential configuration and includes a flange 210 that is configured to contact an inner surface of an abdominal wall of a patient (FIG. 1D). This configuration of flanges 208, 210 maintains the port 200 in a substantially fixed position when the port 200 is positioned within an incision of a patient. One example of a port 200 is disclosed in commonly assigned U.S. patent application Ser. No. 12/244,024 filed, Oct. 2, 2008 the entire contents of which are hereby incorporated by reference herein.

In use, port 200 may be inserted into the open end of the distal end 110 and pushed into the longitudinal slot 114 toward the proximal end 108 (FIG. 1B). Once port 200 is inserted into the longitudinal slot 114, housing 102 may then be inserted into an opening or incision made within a tissue "T" of a patient (FIG. 1C). After housing 102 is properly positioned into the incision, the port 200 may be disengaged from the housing 102 and into the incision where the port 200 will return to its non-compressed condition such that the port 200 is securely positioned within the incision (FIG. 1D). In an embodiment, the push rod 120 may be employed to push the port 200 through the longitudinal slot 114 and from the open distal end 110. Once the port 200 is securely positioned within the incision, one or more types of surgical instruments, e.g., endoscope, may be inserted through the one or more apertures 202.

With reference to FIGS. 2A-2D, and initially with reference to FIG. 2A, an embodiment of a port introducer 300 is shown. In the embodiment illustrated in FIGS. 2A-2D, port introducer 300 includes an introducer assembly 400 that is suitable for use with port 200. The components of port introducer 300 may be formed from any of the hereinbefore disclosed materials.

Introducer assembly 400 is substantially similar to the introducer assembly 100 described above. So as not to obscure the present disclosure with redundant information, only those features unique to introducer assembly 400 will described hereinafter.

Unlike the housing 102, a portion of an elongated introducer or housing 402 is movable between a first or generally open position for receiving at least a portion of the port 200 to a second or generally approximated position for securing and moving the port 200 to a compressed state. With this purpose in mind, the housing 402 includes proximal and distal faces 450 and 452, respectively, and defines a longitudinal axis "A-A." Housing 402 includes a slotted tube configuration defined by two pivotably coupled outer wall segments 402a and 402b. In the embodiment illustrated in FIGS. 2A-2D, a hinge 406, or the like, operably couples the outer wall segments 402a and 402b to each other. The hinge 406 facilitates movement of the housing 402 between the first and second positions. Hinge 406 may be any suitable type of hinge, e.g., living, pinned, strap, and so forth. In the embodiment illustrated in FIGS. 2A-2D, hinge 406 is a living hinge 406 that extends the length of the housing 402 along the distal face 450a thereof.

In an embodiment, one or more locking members 420, e.g., clamp, latch, drawstring, etc., may operably couple to or be operably associated with the housing 402. The locking member(s) may be configured to allow the outer wall segments 402a and 402b to selectively move between the first and second positions and substantially maintain the hinge 406 in the first position during insertion of the housing 402 into an incision. In the embodiment illustrated in FIGS. 2A-2D, the locking member 420 is disposed along the proximal face 450 adjacent a medial portion of the housing 402, see FIG. 2A, More particularly, a drawstring 422 is operably disposed on outer wall segment 402a and receivable within a corresponding receiving structure 424 operably disposed on the outer wall segment 402b. In use, the drawstring 422 is threaded through the receiving structure 424 and manipulated by a user to substantially maintain the hinge 406 in the first position during insertion of the housing 402 into an incision.

Alternatively, the housing 402 may be devoid of a locking member 420 and during insertion of the housing 402 into an incision a user may simply grasp each of the outer wall segments 402a and 402b such that the hinge 406 is substantially maintained in the first position.

In use, outer wall segments 402a and 402b may be in the first position (FIG. 2A). With housing segments 402a and 402b in the first position, port 200 may be positioned between the outer wall segments 402a and 402b, and the outer wall segments 402a and 402b may be moved to the second position. Once port 200 is inserted into the housing, the housing 402 may then be inserted into an opening or incision made within a tissue "T" of a patient (FIG. 2C). After housing 402 is properly positioned into the incision, the port 200 may be disengaged from the housing 402 and into the incision where the port 200 will return to its non-compressed condition such that the port 200 is securely positioned within the incision (FIG. 2D). In an embodiment, the outer wall segments 402a and 402b may be moved back to the first position after the housing is positioned into the tissue to facilitate disengaging the port 200 from the housing 402. Alternatively, or in combination therewith, the push rod 120 may be employed to push the port 200 through the longitudinal slot 414 and from the open distal end 410. Once the port 200 is securely positioned within the incision, one or more types of surgical instruments, e.g., endoscope, may be inserted through the one or more apertures 202.

With reference to FIGS. 3A-3E, and initially with reference to FIG. 3A, an embodiment of a port introducer 500 is shown. In the embodiment illustrated in FIGS. 3A-3E, port introducer 500 includes an introducer assembly 600 that is suitable for use with port 200. The components of port introducer mechanism 500 may be formed from any of the hereinbefore disclosed materials.

Introducer assembly 600 includes an elongated introducer or housing 602 configured to receive, compress and releasably secure the port 200 therein. With this purpose in mind, housing 602 includes an outer wall segment 606 defining a longitudinal axis "A-A." Housing 602 including outer wall segment 606 includes a 'shoe horn" like configuration. More particularly, housing 602 includes open (or trailing) proximal and distal (or leading) ends 608 and 610, respectively. A relatively flat distal face 652 extends along a length of the housing 602. A longitudinal channel or slot 614 is disposed adjacent a proximal face 650 and extends along the length of the housing 602 from the proximal end 608 to the distal end 610 such that the housing 602 includes an oval, generally "C" like configuration (see FIG. 3B, for example). A pair of top edges 614a and 614b extend along the length of the longitudinal slot 614 and run parallel to the longitudinal axis "A-A" (see FIG. 3A in conjunction with FIG. 3B). The longitudinal slot 614 facilitates loading and unloading of the port 200 into the distal end 610 of the housing 102. The longitudinal slot 614 is proportioned to move the port 200 toward a compressed state as the port 200 is pushed within the longitudinal slot 614 from the distal end 610 of the housing 602 toward the proximal end 608 of the housing 602.

A handle section 620 operably couples to the proximal end 608. Handle section 620 may operably couple to the proximal end 608 of the housing by any suitable means. In the embodiment illustrated in FIGS. 3A-3D, handle section 620 is monolithically formed with the housing 602. In embodiments, handle section 620 may be joined to housing 602 via welding, soldering, brazing, and so forth. Alternatively, handle section 620 may operably couple to the housing 620 via a rivet, bolt, screw, and so forth. The handle section 620 includes a "ladle" like configuration with one or more curved surfaces. More particularly, handle section 620 includes a generally arcuate or curved (e.g., convex) proximal end 622 and a generally arcuate or curved (e.g., concave) distal end 625. A portion 626 of the proximal end 622 serves as surface for a user to grip. A portion 628 of the distal end 624 serves as a shoulder that pushes against the port 200 and maintains the port 200 within the housing 602, such as, for example, during insertion the housing 602 into the tissue tract.

In use, port 200 may be positioned within the housing 602 (FIG. 3A). Once port 200 is inserted into the housing 602, the housing 602 may then be inserted into an opening or incision made within a tissue "T" of a patient (FIG. 3C). After housing 602 is properly positioned into the incision, the port 200 may be disengaged from the housing 602 and into the incision where the port 200 will return to its non-compressed condition such that the port 200 is securely positioned within the incision (FIG. 3D). In an embodiment, the push rod 120 may be employed to push the port 200 through the longitudinal slot 614 and from the open distal end 610. Once the port 200 is securely positioned within the incision, one or more types of surgical instruments, e.g., endoscope, may be inserted through the one or more apertures 202.

With reference to FIGS. 4A-4G, and initially with reference to FIG. 4A, an embodiment of a port introducer 700 is shown. In the embodiment illustrated in FIGS. 4A-4G, port introducer 700 includes an introducer assembly 800 that is suitable for use with port 200. The components of port introducer mechanism 700 may be formed from any of the hereinbefore disclosed materials.

Introducer assembly 800 includes an elongated introducer or housing 802. In the embodiment illustrated in FIG. 4A-4G, housing 802 is of a unitary construction formed by any of the aforementioned manufacturing methods and from any of the aforementioned materials. In embodiments, housing 802 is formed from one or more elastomeric materials, such as, for example, polypropylene, polyethylene, etc. In the embodiment illustrated in FIGS. 4A-4D, a portion (e.g., a rigid portion 804) of the housing 802 may be formed from a material that is substantially rigid and a portion (e.g., a flexible portion 806) of the housing 802 may be formed from a material that is substantially flexible (e.g., polyethylene). The significance of housing 802 having substantially rigid and flexible portions 804 and 806, respectively, described in greater detail below. As described hereinabove with respect to any of the aforementioned housing (e.g., 102), in embodiments, housing 802, or portion thereof, may be coated with or formed from any of the aforementioned lubricious materials 104.

Housing 802 is configured to receive, compress and releasably secure the port 200 therein. With this purpose in mind, housing 802 includes a substantially rigid portion 804 and supporting a flexible portion 806 forming an outer wall segment (FIG. 4A-1). Rigid portion 804 extends the length of the housing 802 and includes a generally "banana" like configuration (see FIGS. 4A and 4B, where FIG. 4B illustrates the rigid portion 804 separated from the flexible portion 806).

Rigid portion 804 forms a distal end 810 of housing 802 (FIGS. 4A, 4B and 4C, where FIG. 4C illustrates the rigid portion 806 separated from the flexible portion 804). Rigid portion 804 defines and/or includes a rigid "backbone" 812 that extends at least partially along the length of the rigid portion 804 (as best seen in FIG. 4C). The rigid "backbone" 812 provides additional structural integrity for the housing 802. Flexible portion 806 operably couples to the rigid portion 804. In the embodiment illustrated in FIGS. 4A-4G, flexible portion 806 is overmolded to the rigid portion 804 (FIG. 4A$_{-1}$) and substantially encases the rigid portion 804. Flexible portion 806 extends substantially the length of the rigid portion 804. Flexible portion 806 is movable between a first position for securing the port 200 therein (see FIG. 4A-1 in combination with FIG. 4D, for example) to a second position for facilitating removal of the housing 802 from a tissue tract (shown phantomly in FIG. 4A$_{-1}$). With this purpose in mind, flexible portion 806 includes two generally upright collapsible outer sidewalls 814 and 816 laterally spaced apart from each other and culminating adjacent the distal end 810. The outer sidewalls 814 and 816 are configured to collapse when the port 200 is not positioned within the housing 802 and a force is applied to the outer sidewalls 814 and 816, such as, for example, when the housing 802 is being removed from a tissue tract. The flexible member 806 including outer sidewalls 814 and 816 form a longitudinal slot 818 extending at least partially the length of the housing 802. Longitudinal slot 818 functions in a manner similar to that of the previously described slots, e.g., longitudinal slot 114. Each of the outer sidewalls 814 and 816 includes relatively curved top edges 840 and 842, respectively. Curved top edges 840 and 842 facilitate loading of the port 200 within the housing 802. Flexible member 806 including outer sidewalls 814 and 816 together with rigid portion 804 define a proximal end 820 that includes an opening 822 dimensioned to securely receive a portion (e.g., a distal end 206) of the surgical port 200. Proximal end 820 is dimensioned to move the port 200 toward a compressed state as the port 200 is pushed from the proximal end 820 of the housing 802 toward the distal end 810 of the housing 802. Distal end 810 includes a relatively blunt tip 824. Alternatively, distal end 810 may include a relatively sharp tip configuration (not explicitly shown).

A retrieval structure 828 operably couples the distal end 810 (FIG. 4A). Retrieval structure 828 couples to an aperture 830 located adjacent tip 824. The retrieval structure 828 may be any suitable structure including but not limited suture, string, filament, and so forth. In the embodiment illustrated in FIGS. 4A-4G, retrieval structure is a suture 828 including an end 834 that is looped through the opening 830 and subsequently knotted. In an embodiment, suture 828 may be operably coupled to housing 802 by other suitable coupling means, e.g., adhesives, over-molding, and so forth. Suture 828 may have any suitable length. In the embodiment illustrated in FIGS. 4A-4G, suture 828 includes a length that allows the suture 828 to remain outside the tissue tract after the housing 802 is pushed into and completely through the tissue tract, such that the suture 828 may be employed to pull the housing 802 out of and from the tissue tract, described in greater detail below.

In an embodiment, surgical instrument may be employed to disengage the housing 802 from the surgical port 200 when the housing 802 is positioned within a tissue tract or an incision of the patient. To this end, a surgical instrument in the form of a push rod 120 or the like is receivable within one or more of the openings 202 of the port 200.

In use, the port 200 may be positioned within the proximal end 820 of the housing 802. Once port 200 is secured to the housing 802, distal end 810 of housing 802 may then be inserted into an opening or incision made within a tissue "T" of a patient (FIG. 4E). After housing 802 is inserted into the incision, the port 200 is disengaged, e.g., via a twisting action of the housing 802, from the housing 802, where the port 200 will return to its non-compressed condition such that the port 200 is securely positioned within the incision (see FIG. 4F). In an instance where, the housing 802 is completely inserted through the incision (as shown in FIG. 4F, for example), the housing 802 may be disengaged from the port 206 via one or more surgical instruments, e.g., a push rod 120. In this instance, the suture 832 may be employed to retrieve the housing 802 (FIG. 4G). During extraction of the housing 802 from the incision, the collapsible walls 814 and 816 will collapse or "fold" to the second position, shown in phantom in FIGS. 4A$_{-1}$ and 4G, facilitating removal of the housing from the tissue tract.

With reference to FIGS. 4H-4J an alternate embodiment of a port introducer 700 is shown designated 700a. Port introducer 700a is substantially similar to port introducer 700. So as not to obscure the present disclosure with redundant information only those features unique to port introducer 700a will be described herein.

In the embodiment illustrated in FIGS. 4H-4J, an elongated introducer or housing 802a includes one or more rigid supports or fingers 875 configured to provide added structural integrity to housing 802a and/or a flexible portion 806a, e.g., collapsible outer sidewalls 814a and 816a, operably associated with the housing 802a. In the illustrated embodiment, housing 802a includes a pair of fingers 875. Fingers 875 operably couple to a distal end 810a of a rigid portion 804a and extend proximally toward a proximal end 820a of rigid portion 804a. In the embodiment illustrated in FIGS. 4H-4J, fingers 875 are disposed above a rigid backbone 812a and encased by flexible member 806a, see FIG. 4I in combination with FIG. 4H-1. More particularly, fingers 875 are in spaced apart relation relative to each other and are laterally disposed on opposite sides of a rigid backbone 812a, see FIG. 4H-1 in combination with FIG. 4J. Operation of introducer 800a including fingers 875 is substantially similar to that of introducer 800. One distinguishing feature of the introducer 800a when compared to introducer 800 is that the fingers 875 of housing 802a add an amount of predetermined rigidity to the collapsible walls 814a and 816a.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A surgical apparatus for permitting access to tissue, which comprises:
    an elongated introducer including a retractor segment and an outer wall segment defining a longitudinal axis and a longitudinal port passage extending therethrough, the outer wall segment having a longitudinal slot in communication with the port passage, the elongated introducer dimensioned for at least partial introduction within an opening in the tissue, the retractor segment disposed distal of the outer wall segment, the retractor segment extending radially outward from a distal end of the outer wall segment to retract the opening in the tissue; and
    a surgical port including a port body having leading and trailing ends, an intermediate segment disposed between the leading and trailing ends, and at least one passageway for reception and passage of a surgical instrument, the port body movable along the entire elongated introducer with one of the leading or trailing ends disposed within the port passage and with the intermediate segment extending through the longitudinal slot, the other one of the leading or trailing ends external to the elongated introducer when the one of the leading or trailing ends is advanced along the entire port passage of the elongated introducer, the port body dimensioned to be advanced within the port passage for deployment through the opening in the tissue as generally directed by the elongated introducer, the port body comprising a compressible material adapted to transition from a compressed state when mounted to the elongated introducer to a released state when deployed from the elongated introducer.

2. The surgical apparatus according to claim 1 wherein the retractor segment defines an arcuate profile.

3. The surgical apparatus according to claim 1 wherein the outer wall segment of the elongated introducer is substantially arcuate along a major portion of the length thereof.

4. The surgical apparatus according to claim 1 wherein the retractor segment defines a general hook-shape and is arranged in oblique relation with the longitudinal axis.

5. The surgical apparatus according to claim 1 including a pusher member at least partially disposed within the longitudinal port passage of the elongated introducer, the pusher member adapted for longitudinal advancement to engage and deploy the port body from the introducer and through the opening in the tissue.

6. The surgical apparatus according to claim 1 wherein the elongated introducer includes a handle mounted to the outer wall segment, the handle dimensioned for engagement by a user.

7. The surgical apparatus according to claim 1 wherein the elongated introducer is substantially rigid.

8. The surgical apparatus according to claim 1 wherein at least a portion of the longitudinal slot is coated with a lubricious material.

9. The surgical apparatus according to claim 1 wherein a leading end of the elongated introducer is substantially open and a trailing end is closed.

* * * * *